United States Patent [19]

Gericke et al.

[11] Patent Number: 5,143,924
[45] Date of Patent: Sep. 1, 1992

[54] OXODIHYDROPYRIDYL CHROMAN DERIVATIVES

[75] Inventors: Rolf Gericke, Seeheim; Manfred Baumgarth; Ingeborg Lues, both of Darmstadt; Rolf Bergmann, Reichelsheim; Jacques De Peyer, Bern, all of Fed. Rep. of Germany

[73] Assignee: Merck Patent Gesellschaft mit Beschraenkter Haftung, Darmstadt, Fed. Rep. of Germany

[21] Appl. No.: 555,700

[22] Filed: Jul. 23, 1990

[30] Foreign Application Priority Data

Jul. 24, 1989 [DE] Fed. Rep. of Germany ....... 3924417

[51] Int. Cl.$^5$ ............................................. C07D 405/12
[52] U.S. Cl. .................................... 514/337; 514/253; 514/256; 514/269; 514/272; 514/275; 514/422; 514/456; 544/230; 544/238; 544/298; 544/318; 544/319; 544/405; 546/269; 548/517; 549/401; 549/404
[58] Field of Search .......................... 546/269; 514/337

[56] References Cited

U.S. PATENT DOCUMENTS

| | | | |
|---|---|---|---|
| 3,707,474 | 12/1972 | Razdan et al. | 546/269 |
| 3,947,462 | 3/1976 | Arendsen et al. | 546/269 |
| 3,960,879 | 6/1976 | Fake | 546/269 |
| 3,973,023 | 8/1976 | Fake | 514/337 |
| 4,237,162 | 12/1980 | Kabbe | 546/269 |
| 4,486,428 | 12/1984 | Eggler et al. | 546/269 |
| 4,782,083 | 11/1988 | Cassidy et al. | 514/337 |
| 4,954,518 | 9/1990 | Takano et al. | 514/337 |
| 4,971,982 | 11/1990 | Attwood et al. | 546/269 |
| 5,013,853 | 5/1991 | Gericke | 546/269 |
| 5,043,344 | 8/1991 | Englert | 546/269 |
| 5,071,871 | 12/1991 | Blarer et al. | 514/456 |

FOREIGN PATENT DOCUMENTS

| | | | |
|---|---|---|---|
| 0273262 | 10/1987 | European Pat. Off. | . |
| 0296975 | 12/1988 | European Pat. Off. | 546/269 |
| 0340718 | 11/1989 | European Pat. Off. | . |
| 0363883 | 4/1990 | European Pat. Off. | 546/269 |
| 0400430 | 12/1990 | European Pat. Off. | 544/238 |

OTHER PUBLICATIONS

Buckle et al., Chem. Abstr. vol. 113 Entry 6311a (1990).

*Primary Examiner*—Donald G. Daus
*Attorney, Agent, or Firm*—Millen, White & Zelano

[57] ABSTRACT

Novel chroman derivatives of the formula I

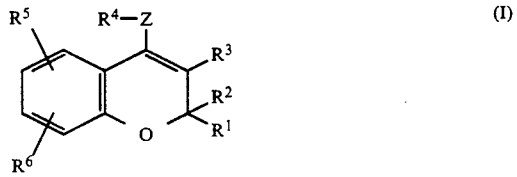

in which
$R^1$ to $R^6$ and Z have the meanings given in Patent Claim 1, and their salts show effects on the cardiovascular system and can be used for the treatment or prophylaxis of cardiac insufficiency, angina pectoris, high blood pressure, incontinence and alopecia.

12 Claims, No Drawings

OXODIHYDROPYRIDYL CHROMAN DERIVATIVES

SUMMARY OF THE INVENTION

The invention relates to novel chroman derivatives of the formula I

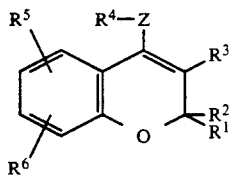

in which
$R^1$ is A,
$R^2$ is H or A,
$R^1$ and $R^2$ together are also alkylene having 3–6 C atoms,
$R^3$ is CHO or $CH_2OH$,
$R^4$ is a pyridyl, pyridazinyl, pyrimidinyl, pyrazinyl, oxodihydropyridyl, oxodihydropyridazinyl, oxodihydropyrimidinyl, oxodihydropyrazinyl, 2-pyrrolidinon-1-yl or 3-oxocyclopenten-1-yl radical which is unsubstituted, monosubstituted or disubstituted by A, F, Cl, Br, I, OH, OA, OAc, SH, $NO_2$, $NH_2$, AcNH, COOH and/or COOA,
$R^5$ and $R^6$ are each H, A, HO, AO, CHO, ACO, ACS, HOOC, AOOC, AO-CS, ACOO, A-CS-O, hydroxyalkyl, mercaptoalkyl, $NO_2$, $NH_2$, NHA, $NA_2$, CN, F, Cl, Br, I, $CF_3$, ASO, $ASO_2$, AO-SO, $AO-SO_2$, AcNH, AO-CO-NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitroalkyl, cyanoalkyl, A-C(=NOH) or A-C(=$NNH_2$),
Z is O, S, NH or a bond,
A is alkyl having 1–6 C atoms, -alkyl is alkylene having 1–6 C atoms and
Ac is alkanoyl having 1–8 C atoms or aroyl having 7–11 C atoms
and their salts.

The invention was based on the object of finding novel compounds having useful properties, in particular those which can be used for the preparation of medicaments.

It has been found that the compounds of the formula I and their physiologically acceptable salts possess, combined with good tolerability, useful pharmacological properties. Thus, they show effects on the cardiovascular system, it usually being possible to observe a selective effect on the coronary system at lower doses and a hypotensive effect at higher doses. In the coronary system, for example, decreases in resistance and increases in flow occur, the influence on the heart rate remaining low. Furthermore, the compounds show a relaxant effect on various smooth muscle organs (gastrointestinal tract, respiratory system and uterus). The effects of the compounds can be determined with the aid of methods which are known per se, as are given, for example, in EP-A1-76,075, EP-A1-173,848 or AU-A-45,547/85 (Derwent Farmdoc No. 86081769) and by K. S. Meesmann et al., Arzneimittelforschung 25 (11), 1975, 1770–1776. Suitable experimental animals are, for example, mice, rats, guinea-pigs, dogs, cats, apes or pigs.

The compounds can therefore be used as active medicament compounds in human and veterinary medicine. In addition, they can be used as intermediates for the preparation of further active medicament compounds.

In the formulae given, A is a preferably unbranched alkyl group having 1–6, preferably 1–4, in particular 1, 2 or 3 C atoms, in detail preferably methyl, in addition preferably ethyl, propyl, isopropyl, butyl, isobutyl, and furthermore preferably sec.-butyl, tert.-butyl, pentyl, isopentyl (3-methylbutyl), hexyl or isohexyl (4-methylpentyl).

If $R^1$ and $R^2$ together are alkylene, the alkylene group is preferably unbranched, in detail preferably —($CH_2$)n—, where n is 3, 4, 5 or 6.

The group "-alkyl" preferably stands for —$CH_2$— or —$CH_2CH_2$—.

Ac is preferably alkanoyl having 1–6, in particular 1, 2, 3 or 4 C atoms, in detail preferably formyl or acetyl, furthermore preferably propionyl, butyryl, isobutyryl, pentanoyl or hexanoyl, and in addition preferably benzoyl, o-, m- or p-toluyl, 1- or 2-naphthoyl.

$R^1$ and $R^2$ are preferably each alkyl, in particular each methyl or ethyl, preferably each methyl; $R^1$ and $R^2$ together are furthermore preferably —($CH_2$)$_4$— or —($CH_2$)$_5$—.

Z is preferably O or a bond.

The group $R^4$-Z is preferably 1,2-dihydro-2-oxo-1-pyridyl, in addition 2-hydroxy-4-pyridyloxy (=1,2-dihydro-2-oxo-4-pyridyloxy), 6-hydroxy-3-pyridazinyloxy (1,6-dihydro-6-oxo-3-pyridazinyloxy), 2- 3- or 4-pyridyloxy, 1,6-dihydro-3-hydroxy-6-pyridazinon-1-yl, 1,2-dihydro-4-hydroxy-2-oxo-1-pyridyl, 1,6-dihydro-1-methyl-6-oxo-3-pyridazinyloxy, 1,6-dihydro-1-ethyl-6-oxo-3-pyridazinyloxy, 2-pyrrolidinon-1-yl or 3-oxocyclopenten-1-yloxy.

In $R^5$ and $R^6$, the following are preferably:
A: methyl, and in addition ethyl;
AO: methoxy, and in addition ethoxy;
ACO: acetyl, and in addition propionyl;
ACS: thioacetyl, and in addition thiopropionyl;
AOOC: methoxycarbonyl, and in addition ethoxycarbonyl;
AO-CS: methoxy-thiocarbonyl, and in addition ethoxy-thiocarbonyl;
ACOO: acetoxy, and in addition propionoxy;
ACSO: thio(no)acetoxy, and in addition thio(no)propionoxy;
hydroxyalkyl: hydroxymethyl or 1- or 2-hydroxyethyl;
mercaptoalkyl: mercaptomethyl or 1- or 2-mercaptoethyl;
NHA: methylamino, and in addition ethylamino;
$NA_2$: dimethylamino, and in addition diethylamino;
ASO: methylsulfinyl, and in additional ethylsulfinyl;
$ASO_2$: methylsulfonyl, an din addition ethylsulfonyl;
AO-SO: methoxy-sulfinyl, and in addition ethoxysulfinyl;
$AO-SO_2$: methoxy-sulfonyl, and in addition ethoxysulfonyl;
Ac-NH: acetamido, and in addition formamido, propionamido or benzamido;
AO-CO-NH: methoxycarbonylamino, and in addition ethoxycarbonylamino;
HANSO: methylaminosulfinyl, and in addition ethylaminosulfinyl;
$A_2NSO$: dimethylaminosulfinyl, and in addition diethylaminosulfinyl;
$HANSO_2$: methylaminosulfonyl, and in addition ethylaminosulfonyl;

$A_2NSO_2$: dimethylaminosulfonyl, and in addition diethylaminosulfonyl;
HANCO: N-methylcarbamoyl, and in addition N-ethylcarbamoyl;
$A_2NOC$: N,N-dimethylcarbamoyl, and in addition N,N-diethylcarbamoy;
HANCS: N-methylthiocarbamoyl, and in addition N-ethylthiocarbamoyl;
$A_2NCS$: N,N-dimethylthiocarbamoyl, and in addition N,N-diethylthiocarbamoyl;
ASONH: methylsulfinylamino, and in addition ethylsulfinylamino;
$ASO_2NH$: methylsulfonylamino, and in addition ethylsulfonylamino;
AOSONH: methoxysulfinylamino, and in addition ethoxysulfinylamino;
$AOSO_2NH$: methoxysulfonylamino, and in addition ethoxysulfonylamino;
ACO-alkyl: 2-oxopropyl, 2-oxobutyl, 3-oxobutyl, 3-oxopentyl;
Nitroalkyl: nitromethyl, 1- or 2-nitroethyl;
Cyanoalkyl: cyanomethyl, 1- or 2-cyanoethyl;
A-C(=NOH): 1-oximinoethyl, and in addition 1-oximinopropyl;
A-C(=NNH$_2$) 1-hydrazinoethyl, and in addition 1-hydrazinopropyl.

The radicals $R^5$ and $R^6$ are preferably in the 6- and 7-position of the chroman system. However, they may also be in the 5- and 6-, 5- and 7-, 5- and 8-, 6- and 8- and 7- and 8position.

One of the radicals $R^5$ and $R^6$ is preferably H, whereas the other is different from H. This other radical is preferably in the 6-position, but also in the 5-, 7- or 8-position, and is preferably CN or $NO_2$, in addition preferably CHO, ACO (in particular acetyl), AOOC (in particular methoxycarbonyl or ethoxycarbonyl), ACOO (in particular acetoxy), and furthermore preferably F, Cl, Br, I, $CF_3$, $H_2NCO$, $H_2NCS$ or $NH_2$.

Accordingly, the invention in particular relates to those compounds of the formula I in which at least one of the radicals mentioned has one of the previously mentioned preferred meanings. Some preferred groups of compounds can be expressed by the formulae Ia to Ii below, which correspond to the formula I and in which the radicals not designated in more detail have the meaning indicated in the formula I, in which however
in Ia—$R^1$ and $R^2$ are each A;
in Ib—$R^1$ and $R_2$ are each $CH_3$;
in Ic—$R^1$ and $R^2$ together are alkylene having 3–6 C atoms;
in Id—$R^4$-Z is 1,2-dihydro-2-oxo-1-pyridyl, 2-hydroxy-4-pyridyloxy, 6-hydroxy-3-pyridazinyloxy, 1,6-hydro-1-methyl-6-oxo-3-pyridazinyloxy, 2-pyrrolidinon-1-yl or 3-oxo-cyclopenten-1-yloxyl;
in Ie—$R^4$—Z is 1,2-dihydro-2-oxo-1-pyridyl;
in If—$R^1$ and $R^2$ are each $CH_3$ or together are —(CH$_2$)$_4$— or —(CH$_2$)$_5$— and
$R^4$-Z is 1,2-dihydro-2-oxo-1-pyridyl, 2-hydroxy-4-pyridyloxy, 6-hydroxy-3-pyridazinyloxy, 1,6-dihydro-1-methyl-6-oxo-3-pyridazinyloxy, 2-pyrrolidonon-1-yl or 3-oxo-cyclopenten-1-yloxy;
in Ig—$R^1$ and $R^2$ are each $CH_3$ and
$R^4$-Z—is 1,2-dihydro-2-oxo-1-pyridyl or 6-hydroxy-3-pyridazinyloxy;
in Ih—$R^1$ and $R^2$ are each $CH_3$ and
$R^4$-Z—is 2-pyrrolidinon-1-yl;
in Ii—$R^1$ and $R^2$ are each $CH_3$ and $R^4$-Z is 1,2-dihydro-2-oxo-1-pyridyl.

Compounds of the formulae I' and Ia' to Ii' are furthermore preferred which correspond to the formulae I and Ia to I, but in which in each case additionally $R^3$ is CHO.

Compounds of the formulae I'' and Ia'' to Ii'' are furthermore preferred which correspond to the formulae I, and Ia to Ii, but in which in each case $R^3$ is $CH_2OH$.

Compounds of the formulae I, I', I'', Ia to Ii, Ta'to Ii' and Ia'' to Ii'' are in addition preferred, in which in each case additionally
(a) $R^5$—is different from H and $R^6$—is H;
(b) $R^5$—is different from H and is in the 6-position and $R^6$—is H;
(c) $R^5$—is $NO_2$, CN, CHO, ACO, HOOC, AOOC, ACOO, F, Cl, Br, I, $CF_3$, $H_2NCO$, $H_2NCS$ or $NH_2$ and $R^6$—is H;
(d) $R^6$—is $NO_2$, CN, CHO, ACO, HOOC, AOOC, ACO, F, Cl, Br, I, $CF_3$, $H_2NCO$, $H_2NCS$ or $NH_2$ and is in the 6-position and $R^6$—is H;
(e) $R^6$—is $NO_2$, CN, CHO, $CH_3CO$, $CH_3OOC$, $C_2H_5OOC$ or $CH_3COO$ and $R^6$—is H;
(f) $R^5$—is $NO_2$, CN, CHO, $CH_3CO$, $CH_3OOC$, $C_2H_5OOC$ or $CH_3COO$ and is in the 6-position and $R^6$—is H;
(g) $R^5$—is $NO_2$ or CN and $R^6$—is H;
(h) $R^5$—is $NO_2$ or CN and is in the 6-position and $R^6$—is H;
(i) $R^5$—is CN and $R^6$—is H;
(j) $R^5$—is CN and is in the 6-position and $R^6$—is H.

Otherwise, the radicals $R^1$ to $R^6$, Z, A, "-alkyl" and Ac above and below have the meanings given in formula I, if not expressly stated otherwise.

The invention in addition relates to a process for the preparation of chroman derivatives of the formula I, characterized in that a compound of the formula II

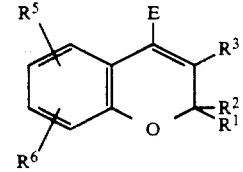

in which
E is Cl, Br, I or a reactively esterified OH group and $R^1$, $R^2$, $R^3$, $R^5$, and $R^6$ have the meanings given in formula I,
is reacted with a compound of the formula III $R^4$—Z—H <span style="float:right">III</span> in which
$R^4$ and Z have the meanings indicated in formula I, or in that for the preparation of a compound of the formula I in which $R^3$ is $CH_2OH$, a compound of the formula I in which $R^3$ is CHO is treated with a reducing agent, and/or in that in a compound of the formula I, one or more of the radicals $R^4$, $R^5$ and/or $R^6$ are converted into other radicals $R^4$, $R^5$ and/or $R^6$ and/or in that a basic or acidic compound of the formula I is converted into one of its salts by treating with an acid or base.

The compounds of the formula I are otherwise prepared by methods which are known per se, as are described in the literature (for example in the standard works such as Houben-Weyl, Methoden der organischen Chemie (Methods of Organic Chemistry), Georg-Thieme Verlag, Stuttgart; Organic Reactions, John Wiley & Sons, Inc., New York; and in the abovementioned patent applications), in particular under reaction conditions which are known and suitable for the reactions mentioned. In this case, use can also be made of variants which are known per se but which are not mentioned in more detail here.

The starting materials may also be formed, if desired, in situ in such a way that they are not isolated from the reaction mixture, but immediately reacted further to give the compounds of the formula I.

Preferably, the compounds of the formula I are prepared by reacting compounds of the formula II with compounds of the formula III, preferably in the presence of an inert solvent at temperatures between about 0° and 150°.

Starting materials of the formula II are novel. Those with $R^3$=CHO and E=Br are preferred. The latter can be prepared by reaction of 2-hydroxyacetophenones of the formula 2-HO—$R^5R^6C_6H_2$—$COCH_3$ with ketones of the formula $R^1$—CO—$R^2$ to give corresponding 2-$R^1$-2-$R^2$-4-chromanones which are optionally substituted in the benzene ring by $R^5$ and $R^6$ and subsequent reaction of the latter with $PBr_3$/dimethylformamide (DMF). The compounds of the formula II where $R^3$=$CH_2OH$ are obtainable from these by reduction.

The starting materials of the formula III are usually known (compare, for example, DE-OS 3,726,261). If they are not known, they can be prepared by methods which are known per set.

In compounds of the formula II possible "reactively esterified OH groups" are in particular esters with alkylsulfonic acids (in which the alkyl group contains 1–6 C atoms) or with arylsulfonic acids (in which the aryl group contains 6–10 C atoms).

During the reaction of II with III, it is expedient to work in the presence of a base. Suitable bases are preferably, hydroxides, carbonates, alkoxides, and also amides of alkali metals or alkaline earth metals, such as NoOH, KOH, Ca(OH)$_2$, Na$_2$CO$_3$, K$_2$CO$_3$, Na methoxide or K methoxide, Na ethoxide or K ethoxide or Na tert.-butoxide or K tert.-butoxide, NaNH$_2$, KNH$_2$, and in addition organic bases such as triethylamine or pyridine, which can also be used in excess and then at the same time can serve as solvent.

Suitable inert solvents are, in particular, alcohols such as methanol, ethanol, osopropanol, n-butanol or tert.-butanol; ethers such as tetrahydrofuran (THF) or dioxane; glycol ethers such as ethylene glycol monomethyl ether or ethylene glycol monoethyl ether (methyl glycol or ethyl glycol), ethylene glycol dimethyl ether (diglyme); amides such as DMF, dimethylacetamide or hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride. Mixtures of these solvents with one another are furthermore suitable.

A particularly preferred procedure consists in reacting a mixture of II, III and excess K$_2$CO$_3$ in DMF at about 40°–70°.

In order to prepare compounds of the formula I in which $R^3$ is $CH_2OH$, aldehydes of the formula I in which $R^3$ is CHO can also be treated with a reducing agent. A complex metal hydride such as NaBH$_4$ or LiBH$_4$ is preferably used and the reaction is carried out in one of the solvents indicated, preferably in an alcohol such as methanol at temperatures between 10° and 50°, preferably between 15° and 30°.

Furthermore, one or more of the radicals $R^4$, $R^5$, and/or $R^6$ can be converted into other radicals $R^4$, $R^5$, and/or $R^6$ in a compound of the formula I.

For example, it is possible to replace an H atom by a halogen atom by means of a halogenation and/or to reduce a nitro group to an amino group and/or to alkylate or acylate an amino or hydroxyl group and/or to convert a cyano group (for example with HCl in water/methanol at 20°–100°) into a carboxyl group or (for example with Raney nickel in water/acetic acid/pyridine in the presence of sodium phosphate) into a formyl group or (for example with KOH in tert.-butanol) into a carbamoyl group or (for example with H$_2$S in pyridine/triethylamine) into a thiocarbamoyl group and/or to dehydrate a carbamoyl group (for example with POCl$_3$) into a cyano group and/or to convert a —CO—NH— group, (for example with P$_2$S$_5$ or with Lawesson reagent in toluene) into a —CS—NH— or —C(SH)=N— group.

Halogenation can be carried out, for example using elemental chlorine or bromine in one of the customary inert solvents at temperatures between about 0° and 30°. If at least one of the substituents $R^5$ and $R^6$ is an electronegative group such as CN or NO$_2$, the chlorination predominantly takes place at the radical $R^4$; otherwise mixtures are usually obtained in which the halogen atoms are in the radical $R^4$ or on the benzene ring.

A primary or secondary amino group and/or an OH group can be converted into the corresponding secondary or tertiary amino group and/or alkoxy group by treating with alkylating agents. Suitable alkylating agents are, for example, compounds of the formulae A-Cl, A-Br or A-I or corresponding sulfuric acid or sulfonic acid esters, such as methyl chloride, bromide or iodide, dimethyl sulfate or methyl p-toluenesulfonate. In addition, for example, one or two methyl groups can be introduced with formaldehyde in the presence of formic acid. The alkylation is preferably carried out in the presence or absence of one of the inert solvents mentioned, for example DMF, at temperatures between about 0° and about 120°, in which case a catalyst can also be present, preferably a base such as potassium tert.-butoxide or NaH.

Suitable acylating agents for the acylation of amino or hydroxyl groups are preferably the halides (for example chlorides or bromides) or anhydrides of carboxylic acids of the formula Ac-OH, for example acetic anhydride, propionyl chloride, isobutyryl bromide, formic acid/acetic anhydride and benzoyl chloride. The addition of a base such as pyridine or triethylamine during the acylation is possible. The acylation is preferably carried out in the presence or absence of an inert solvent, for example a hydrocarbon such as toluene, a nitrile such as acetonitrile, an amide such as DMF or an excess of a tertiary base such as pyridine or triethylamine, at temperatures between about 0° and about 160°, preferably between 20° and 120°. Formulation is also carried out using formic acid in the presence of pyridine.

A base of the formula I can be converted into the respective acid addition salt using an acid. Acids which give physiologically acceptable salts are particularly suitable for this reaction. Thus, inorganic acids can be used, for example sulfuric acid, nitric acid, hydrohalic acids such as hydrochloric acid or hydrobromic acid, phosphoric acids such as orthophosphoric acid, sulfamic acid, and in addition organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and -disulfonic acids, and laurylsulfuric acid. Salts with physiologically unacceptable acids, for example picrates, can be used for purifying the compounds of the formula I.

Acidic compounds of the formula I can be converted into corresponding salts by treating with bases, for example into their Na salts with NaOH.

The compounds of the formula I may possess one or more chiral centres. They can therefore be obtained during their preparation as racemates or also, if optically active starting materials are used, in optically active form. If the compounds have two or more chiral centres, they may be obtained during synthesis as mixtures of racemates from which the individual racemates can be isolated in pure form, for example by recrystallizing from insert solvents.

Racemates obtained can, if desired, be separated mechanically, chemically or biochemically into their enantiomers by methods known per se. Thus, diastereomers can be formed from the racemate by reaction with an optically active resolving agent. Suitable resolving agents for basic compounds of the formula I are, for example, optically active acids, such as the D- and L- forms of tartaric acid, dibenzoyltartaric acid, diacetyltartaric acid, camphanic acid, camphorsulfonic acids, mandelic acid, malic acid or lactic acid. Carbinols (for example I, $R^3$=$CH_2OH$) can in addition be esterified and then resolved with the aid of chiral acylating reagents, for example D- or L-α-methylbenzyl isocyanate (cf. EP-A1-120,428). The different forms of the diastereomers can be separate in a manner known per se, for example by fractional crystallization, and the enantiomers of the formula I can be liberated in a manner known per se from the diastereomers. Resolution of enantiomers is in addition carried out by chromatography on optically active support materials.

The compounds of the formula I and their physiologically acceptable salts can be used for the production of pharmaceutical preparations, in particular in nonchemical ways. In this connection, they can be brought into a suitable form for administration together with at least one solid, liquid and/or semi-liquid excipient or auxiliary and, if desired, in combination with one or more further active compound(s).

The invention in addition relates to agents, in particular pharmaceutical preparations, containing at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical administration and which do not react with the novel compounds, for example water, vegetable oils, benzyl alcohols, polyethylene glycols, glycerol triacetate, gelatin, carbohydrates such as lactose or starch, magnesium stearate, talc, lanolin or petroleum jelly. Tablets, coated tablets, capsules, syrups, elixirs or drops are used in particular for oral administration, suppositories are used in particular for rectal administration, solutions, preferably oily or aqueous solutions, and in addition suspensions, emulsions or implants are used in particular for parenteral administration, and ointments, creams, pastes, lotions, gels, sprays, foams, aerosols, solutions (for example solutions in alcohols such as ethanol or isopropanol, acetonitrile, DMF, dimethylacetamide, 1,2-propanediol or their mixtures with each other and/or with water) or powders are used in particular for topical application. The novel compounds can also be lyophilized and the lyophilizates obtained used, for example, for the production of injectable preparations. Liposomal preparations are in particular also suitable for topical application. The preparations mentioned can be sterilized and/or can contain auxiliaries such as lubricants, preservatives, stabilizers and/or wetting agents, emulsifiers, salts for influencing the osmotic pressure, buffer substances, colorants, flavorings and/or aromatizers. They can, if desired, also contain one or more further active compounds, for example one or more vitamins.

The compounds of the formula I and their physiologically acceptable salts can be administered to humans or animals, in particular mammals such as apes, dogs, cats, rats or mice and can be used in the therapeutic treatment of the human or animal body and also in the control of diseases, in particular in the therapy and/or propylaxis of disturbances of the cardiovascular system, in particular decompensated cardiac insufficiency, angina pectoris, arrhythmia, peripheral or cerebral vessel disorders, and disease conditions which are connected with high blood pressure, and in addition disorders which are connected with changes in the non-vascular musculature, for example asthma or urinary incontinence.

In this connection, the substances according to the invention are usually administered analogously to known antianginals or hypotensives, for example nicorandil or cromakalim, preferably in doses between about 0.01 and 5 mg, in particular between 0.01 and 0.05 mg per dose unit. The daily dose is preferably between about 0.0001 and 0.1, in particular between 0.0003 and 0.01 mg/kg of body weight. The specific dose for each particular patient depends, however, on a variety of factors, for example on the efficacy of the specific compound employed, on the age, body weight, the general state of health, sex, on the food, on the time and route of administration, on the excretion rate, medicament combination and severity of the particular disease to which the therapy applies. One of ordinary skill in the art would clearly understand, with only routine experimentation, how to adjust the dosage amounts for these factors. Oral administration is preferred.

The compounds of the formula I and their salts are in addition suitable, in particular on topical application, for the treatment of alopecia areata. For this purpose, in particular, pharmaceutical preparations are used which are suitable for the topical treatment of the scalp and which are mentioned above. The contain about 0.005 to 10, preferably 0.5 to 3% by weight of at least one compound of the formula I and/or at least one of its salts. Otherwise, these compounds can be used against alopecia in analogy to the statements in WO 88/00822.

All of the compounds disclosed are suitable, to at least a finite extent, for all of the disclosed activities.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 24 417.2, filed Jul. 24, 1989, are hereby incorporated by reference.

In the following examples, "customary working up" means:

Water is added, if necessary; the mixture is extracted using an organic solvent such as ethyl acetate, the organic phase is separated off, dried over sodium sulfate, filtered and evaporated, and the residue is purified by chromatography and/or crystallization.

EXAMPLES

EXAMPLE 1

A mixture of 1.4 g of 2,2-dimethyl-3-formyl-4-bromo-6-cyano-3-chromene (m.p. 124°–125°; obtainable by dropwise addition of a solution of 2,2-dimethyl-5-cyano-5-chromanone in chloroform to a mixture of equal volume parts of DMF and PBr$_3$ in chloroform and subsequent boiling for 11 hours), 0.9 g of 1H-2-pyridone, 3 g of K$_2$CO$_3$ and 20 ml of DMF is stirred at 60° for 1 hour. The mixture is diluted with ethyl acetate and filtered, and customary working up of the filtrate gives 2,2-dimethyl-3-formyl-4-(1,2-dihydro-2-oxo-1-pyridyl)-6-cyano-3-chromene ("A") m.p. 190°–192° C.

The following are obtained analogously:
with 3,6-pyrazinediol (=3-hydroxy-1,6-dihydro-6-pyridazinone):
2,2-Dimethyl-3-formyl-4-(6-oxo-1,6-dihydro-3-pyridazinyloxy)-6-cyano-3-chromene, m.p. 270°–272°
with 2,4-dihydroxypyridine:
2,2-Dimethyl-3-formyl-4-(1,2-dihydro-2-oxo-4-pyridyloxy)-6-cyano-3-chromene
with 2-pyrrolidinone:
2,2-Dimethyl-3-formyl-4-(2-oxo-pyrrolidino)-6-cyano-3-chromene
with 1,3-cyclopentanedione:
2,2-Dimethyl-3-formyl-4-(3-oxo-1-cyclopentenyloxy)-6-cyano-3-chromene.

The following are obtained analogously from the corresponding 3-formyl-4-bromo-3-chromenes:
2,2-Tetramethylene-3-formyl-4-(1,2-dihydro-2-oxo-1-pyridyl)-6-cyano-3-chromene
2,2-Pentamethylene-3-formyl-4-(1,2-dihydro-2-oxo-1-pyridyl)-6-cyano-3-chromene
2,2-Dimethyl-3-formyl-4-(1,2-dihydro-2-oxo-1-pyridyl)-6-nitro-3-chromene
2,2-Dimethyl-3-formyl-4-(1,2-dihydro-2-oxo-1-pyridyl)-6-bromo-3-chromene
2,2-Dimethyl-3-formyl-4-(1,2-dihydro-2-oxo-1-pyridyl)-6-acetyl-3-chromene
2,2-Dimethyl-3-formyl-4-(1,2-dihydro-2-oxo-1-pyridyl)-6-methoxycarbonyl-3-chromene
2,2-Dimethyl-3-formyl-4-(6-oxo-1,6-dihydro-3-pyridazinyloxy)-6-nitro-3-chromene
2,2-Dimethyl-3-formyl-4-(6-oxo-1,6-dihydro-3-pyridazinyloxy)-6-bromo-3-chromene
2,2-Dimethyl-3-formyl-4-(6-oxo-1,6-dihydro-3-pyridazinyloxy)-6-acetyl-3-chromene
2,2-Dimethyl-3-formyl-4-(6-oxo-1,6-dihydro-3-pyridazinyloxy)-6-methoxycarbonyl-3-chromene
2,2-Dimethyl-3-formyl-4-(1,2-dihydro-2-oxo-4-pyridyloxy)-6-nitro-3-chromene
2,2-Dimethyl-3-formyl-4-(1,2-dihydro-2-oxo-4-pyridyloxy)-6-bromo-3-chromene
2,2-Dimethyl-3-formyl-4-(1,2-dihydro-2-oxo-4-pyridyloxy)-6-acetyl-3-chromene
2,2-Dimethyl-3-formyl-4-(1,2-dihydro-2-oxo-4-pyridyloxy)-6-methoxycarbonyl-3-chromene
2,2-Dimethyl-3-formyl-4-(2-oxo-pyrrolidino)-6-nitro-3-chromene
2,2-Dimethyl-3-formyl-4-(2-oxo-pyrrolidino)-6-bromo-3-chromene
2,2-Dimethyl-3-formyl-4-(2-oxo-pyrrolidino)-6-acetyl-3-chromene
2,2-Dimethyl-3-formyl-4-(2-oxo-pyrrolidino)-6-methoxycarbonyl-3-chromene
2,2-Dimethyl-3-formyl-4-(3-oxo-cyclopentenyloxy)-6-nitro-3-chromene
2,2-Dimethyl-3-formyl-4-(3-oxo-cyclopentenyloxy)-6-bromo-3-chromene
2,2-Dimethyl-3-formyl-4-(2-oxo-pyrrolidino)-6-acetyl-3-chromene
2,2-Dimethyl-3-formyl-4-(2-oxo-pyrrolidino)-6-methoxycarbonyl-3-chromene.

Example 2

200 mg of NaBH$_4$ are added to a solution of 300 mg of ("A") in 20 ml of methanol. The mixture is evaporated, and customary working up gives 2,2-dimethyl-3-hydroxymethyl-4-(1,2-dihydro-2-oxo-1-pyridyl)-6-cyano-3-chromene, m.p. 190°–192°.

The following are obtained analogously by reduction of the corresponding 3-formyl compounds:
2,2-Dimethyl-3-hydroxymethyl-4-(6-oxo-1,6-dihydro-3-pyridazinyloxy)-6-cyano-3-chromene
2,2-Dimethyl-3-hydroxymethyl-4(1,2-dihydro-2-oxo-4-pyridyloxy)-6-cyano-3-chromene
2,2-Dimethyl-3-hydroxymethyl-4(2-oxopyrrolidino)-6-cyano-3-chromene
2,2-Dimethyl-3-hydroxymethyl-4(3-oxo-1-cyclopentenyloxy)-6-cyano-3-chromene
2,2-Tetramethylene-3-hydroxymethyl-4-(1,2-dihydro-2-oxo-1-pyridyl)-6-cyano-3-chromene
2,2-Pentamethylene-3-hydroxymethyl-4-(1,2-dihydro-2-oxo-1-pyridyl)-6-cyano-3-chromene
2,2-Dimethyl-3-hydroxymethyl-4(1,2-dihydro-2-oxo-1-pyridyl)-6-nitro-3-chromene
2,2-Dimethyl-3-hydroxymethyl-4(1,2-dihydro-2-oxo-1-pyridyl)-6-bromo-3-chromene
2,2-Dimethyl-3-hydroxymethyl-4(1,2-dihydro-2-oxo-1-pyridyl)-6-acetyl-3-chromene
2,2-Dimethyl-3-hydroxymethyl-4(1,2-dihydro-2-oxo-1-pyridyl)-6-methoxycarbonyl-3-chromene
2,2-Dimethyl-3-hydroxymethyl-4(6-oxo-1,6-dihydro-3-pyridazinyloxy)-6-nitro-3-chromene
2,2-Dimethyl-3-hydroxymethyl-4(6-oxo-1,6-dihydro-3-pyridazinyloxy)-6-bromo-3-chromene
2,2-Dimethyl-3-hydroxymethyl-4(6-oxo-1,6-dihydro-3-pyridazinyloxy)-6-acetyl-3-chromene
2,2-Dimethyl-3-hydroxymethyl-4(6-oxo-1,6-dihydro-3-pyridazinyloxy)-6-methoxycarbonyl-3-chromene 2,2-Dimethyl-3-hydroxymethyl-4(1,2-dihydro-2-oxo-4-pyridyloxy)-6-nitro-3-chromene
2,2-Dimethyl-3-hydroxymethyl-4(1,2-dihydro-2-oxo-4-pyridyloxy)-6-bromo-3-chromene
2,2-Dimethyl-3-hydroxymethyl-4(1,2-dihydro-2-oxo-4-pyridyloxy)-6-acetyl-3-chromene
2,2-Dimethyl-3-hydroxymethyl-4(1,2-dihydro-2-oxo-4-pyridyloxy)-6-methoxycarbonyl-3-chromene
2,2-Dimethyl-3-hydroxymethyl-4(2-oxo-pyrrolidino)-6-nitro-3-chromene
2,2-Dimethyl-3-hydroxymethyl-4(2-oxo-pyrrolidino)-6-bromo-3-chromene
2,2-Dimethyl-3-hydroxymethyl-4(2-oxo-pyrrolidino)-6-acetyl-3-chromene
2,2-Dimethyl-3-hydroxymethyl-4(2-oxo-pyrrolidino)-6-methoxycarbonyl-3-chromene
2,2-Dimethyl-3-hydroxymethyl-4(3-oxo-1-cyclopentenyloxy)-6-nitro-3-chromene
2,2-Dimethyl-3-hydroxymethyl-4(2-oxo-pyrrolidino)-6-bromo-3-chromene
2,2-Dimethyl-3-hydroxymethyl-4(2-oxo-pyrrolidino)-6-acetyl-3-chromene
2,2-Dimethyl-3-hydroxymethyl-4(2-oxo-pyrrolidino)-6-methoxycarbonyl-3-chromene.

Example 3

A solution of 1 g of 2,2-dimethyl-3-hydroxymethyl-4-(1,2-dihydro-2-oxo-1-pyridyl)-6-nitro-3-chromene in 25 ml of methanol is hydrogenated on 0.5 g of 5% Pd-C at 20° C. and at 1 bar until hydrogenation is complete. The mixture is filtered, evaporated and 2,2-dimethyl-3-hydroxymethyl-4-(1,2-dihydro-2-oxo-1-pyridyl)-6-amino-3-chromene is obtained.

Example 4

A solution of 1 g of 2,2-dimethyl-3-hydroxymethyl-4-(1,2-dihydro-2-oxo-1-pyridyl)6-amino-3-chromene in 15 ml of formic acid and 1 ml of pyridine is boiled for 24 hours and evaporated. After customary working up, 2,2-dimethyl-3-hydroxymethyl-4-(1,2-dihydro-2-oxo-1-pyridyl)-6-formamido-3-chromene is obtained.

Example 5

A mixture of 1 g of 2,2-dimethyl-3-hydroxymethyl-4-(1,2-dihydro-2-oxo-1-pyridyl)-6-amino-3-chromene, 10 ml of acetic anhydride and 10 ml of pyridine is allowed to stand at 20° C. for 24 hours. The mixture is evaporated, and customary working up gives 2,2-dimethyl-3-hydroxymethyl-4-(1,2-dihydro-2-oxo-1-pyridyl)-6-acetamido-3-chromene.

Example 6

HCl is passed into a boiling solution of 1 g of "A" in 50 ml of methanol and 2 ml of water for 12 hours with stirring. The mixture is allowed to cool and to stand overnight. The 2,2-dimethyl-3-formyl-4-(1,2-dihydro-2-oxo-1-pyridyl)-3-chromene-6-carboxylic acid which precipitates is filtered off.

Example 7

A mixture of 1 g o of "A", 10 g of trisodium phosphate dodecahydrate, 9 ml of pyridine, 9 ml of water, 22 ml of acetic acid and 8 g of Raney-Nickel (water-moist) is stirred at 20° for 3 hours. The mixture is filtered and customary working up gives 2,2-dimethyl-3,6-diformyl-4-(1,2-dihydro-2-oxo-1-pyridyl)-3-chromene.

Example 8

1 g of "A" is dissolved in 15 ml of tert.-butanol and 2 g of powdered KOH are added while stirring and passing in $N_2$. After boiling for 1 hour and customary working up, 2,2-dimethyl-3-formyl-4(1,2-dihydro-2-oxo-1-pyridyl)-6-carbamoyl-3-chromene is obtained.

Example 9

$H_2S$ is passed into a solution of 1 g of "A" in a mixture of 7 pyridine and 7 ml of triethylamine at 20° for 3 hours, and customary working up gives 2,2-dimethyl-3-formyl-4-(1,2-dihydro-2-oxo-1-pyridyl)-6-thiocarbamoyl-3-chromene.

The examples below relate to pharmaceutical preparations which contain compounds of the formula I and/or their physiologically acceptable salts.

Example 1

Tablets

A mixture of 0.2 kg of "A", 136.3 kg of calcium hydrogen phosphate, 15 kg of corn starch, 10 kg of microcrystalline cellulose, 5.5 kg of insoluble polyvinylpyrrolidone (PVP), 1.5 kg of highly disperse silica and 1.5 kg of magnesium stearate is pressed to give tablets in a customary manner. Each 170 mg tablet contains 0.2 mg of active compound.

Example 2

Coated tablets

Tablets are pressed analogously to Example 1, but without the addition of PVP, and are subsequently coated in a customary manner with a coating of sucrose, corn starch, talc, tragacanth or colorant.

Example 3

Lacquered tablets

Tablet cores (170 mg) are pressed from 0.2 kg of 2,2-dimethyl-3-hydroxymethyl-4-(1,2-dihydro-2-oxo-1-pyridyl)-6-cyano-3-chromene, 151.3 kg of lactose, 10 kg of microcrystalline cellulose, 5.5 kg of insoluble PVP, 1.5 kg of highly disperse silica and 1.5 kg of calcium stearate, and are then lacquered in a customary manner so that each lacquered tablet is coated with 3.922 mg of a lacquer which consists of 2.2 mg of hydroxypropylmethyl cellulose, 0.53 mg of polyethylene glycol 400, 0.85 mg of titanium dioxide, 0.12 mg of iron(III) oxide (yellow), 0.002 mg of iron(III) oxide (red) and 0.22 mg of silicone oil.

Example 4

Capsules

Granules are prepared from 10 g of 2,2-dimethyl-3-formyl-4-(6-oxo-1,6-dihydro-3-pyridazinyloxy)-6-cyano-3-chromene, 27.5 kg of lactose, 0.35 kg of hydroxypropylmethyl cellulose and 0.7 kg of corn starch, these are mixed with 0.15 kg of highly disperse silica and 0.3 kg of magnesium stearate and the mixture is poured into hard gelatin capsules in the customary manner so that each capsule contains 0.1 mg of active compound.

Example 5

Ampoules

A solution of 10 g of "A" in 70 l of 1,2-propanediol is made up to 100 l with double-distilled water, sterile filtered, and the solution is poured into 1 ml ampoules, which are then sealed in a sterile manner. Each ampoule contains 0.1 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A chroman compound of formula I

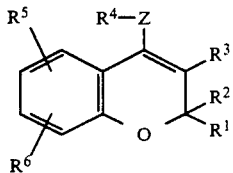

in which
$R^1$ is A,
$R^2$ is H or A, or
$R^1$ and $R^2$ together are also $C_{3-6}$-alkylene,
$R^3$ is CHO or $CH_2OH$,
$R^4$ is oxodihydropyridyl-1-,
$R^5$ is CN,
$R^6$ is H,
Z is O, NH or a bond,
A is $C_{1-6}$-alkyl, -alkyl is $C_{1-6}$-alkylene and Ac is $C_{1-8}$-alkanoyl or $C_{7-11}$-aroyl or a pharmaceutically acceptable salt thereof.

2. A chroman compound of claim 1, wherein $R^1$ and $R^2$ are each A.

3. A chroman compound of claim 1, wherein $R^1$ and $R^2$ are each $CH_3$.

4. A chroman compound of claim 1, wherein $R^1$ and $R^2$ together are $C_{3-6}$-alkylene.

5. A chroman compound of claim 1, wherein $R^4$-Z is 1,2-dihydro-2-oxo-1-pyridyl or 2-hydroxy-4-pyridyloxy.

6. A chroman compound of claim 1, wherein $R^4$-Z is 1,2-dihydro-2-oxo-1-pyridyl.

7. A chroman compound of claim 1, wherein $R^1$ and $R^2$ are each $CH_3$ or together are —$(CH_2)_4$— or —$(CH_2)_5$— and
$R^4$-Z is 1,2-dihydro-2-oxo-1-pyridyl or, 2-hydroxy-4-pyridyloxy.

8. A chroman compound of claim 1, wherein
$R^1$ and $R^2$ are each $CH_3$ and
$R^4$-Z is 1,2-dihydro-2-oxo-1-pyridyl.

9. A chroman compound of claim 1, wherein
$R^1$ and $R^2$ are each $CH_3$ and
$R^4$-Z is 1,2-dihydro-2-oxo-1-pyridyl.

10.
a) 2,2-Dimethyl-3-formyl-4-(1,2-dihydro-2-oxo-1-pyridyl)-6-cyano-3-chromene,
b) 2,2-Dimethyl-3-hydroxymethyl-4-(1,2-dihydro-2-oxo-1-pyridyl)-6-cyano-3-chromene;

11. A pharmaceutical composition comprising a compound of claim 1 and a pharmaceutically acceptable carrier.

12. A method of treating which high blood pressure comprising administering an antihypertensive amount of a compound of claim 1 to a mammal in need thereof.

* * * * *